United States Patent [19]

Hansen

[11] Patent Number: 5,576,420

[45] Date of Patent: Nov. 19, 1996

[54] SUBTILIN VARIANT OF ENHANCED STABILITY AND ACTIVITY

[75] Inventor: J. Norman Hansen, Silver Spring, Md.

[73] Assignee: University of Maryland, College Park, Md.

[21] Appl. No.: 220,033

[22] Filed: Mar. 30, 1994

Related U.S. Application Data

[60] Division of Ser. No. 981,525, Nov. 25, 1992, Pat. No. 5,516,682, which is a continuation-in-part of Ser. No. 214,959, Jul. 5, 1988, Pat. No. 5,218,101.

[51] Int. Cl.$^6$ .......................... C07K 14/32; C12P 21/00; C12N 15/00
[52] U.S. Cl. .................. 530/324; 435/69.1; 435/172.3
[58] Field of Search .................. 435/69.1, 172.3, 435/252.3; 530/300, 324

[56] References Cited

PUBLICATIONS

Banerjee et al., J. Biol. Chem., 263(9):9508–9514 (1988).
Buchmann et al. J. Biol. Chem., 263(31):16260–16266 (1988).
Liu et al., J. Bartenol. 173(22):7387–7390 (1941).
Hansen et al., Noin & Novel Artibiotics, Escom Sci. Publ., Leidon, Germany pp. 287–302 (1991).
Glover et al., Gene Cloning: The mechanics of DNA Manipulation Chapman and Hill LTO, London, England pp. 36–47 (1984).

*Primary Examiner*—Nancy T. Vogel
*Attorney, Agent, or Firm*—Oblon, Spivak, McClelland, Maier, & Neustadt, P.C.

[57] ABSTRACT

A subtilin mutant substituting isoleucine for $Glu_4$ of the native sequence (SEQ ID NO:7) exhibits a 57-fold improvement in stability, resisting modification of the dehydroalanine residue at position 5. This stable mutant exhibits 3–4 times the specific activity, in suppression of bacterial spore outgrowth, of the native bacteriocin. A method for site-specific mutagenesis, as well as the resulting mutant gene, plasmid and transformant is similarly set forth.

11 Claims, 8 Drawing Sheets

```
                                    *
                       xba I
r.b.s.  BstEII         C A
TGAAAGGAGGTCACCAATATGTCAAAGTTCGATGATTTCGATTTGGATGTTGTGAAAGTCTCTAAACAA
                       METSerLysPheAspAspPheAspLeuAspValValLysValSerLysGln Bst BI                   IleAla      Sma I
 T G                     ATTGCA       C G
GACTCAAAAATCACTCCGCAATGGAAAAGTGAATCACTTTGTACACCAGGATGTGTAACTGGTGCATTG
AspSerLysIleThrProGlnTrpLysSerGluSerLeuCysThrProGlyCysValThrGlyAlaLeu
                          1  2  3  4  5  6  7  8  9 10 11 12 13 14 15 16

Bst EII Sna BI
                                               G   CC  TACG
CAAACTTGCTTCCTTCAAACACTAACTTGTAACTGCAAAATCTCTAAATAAGTAAAA CCATTAGCATCA
GlnThrCysPheLeuGlnThrLeuThrCysAsnCysLysIleSerLysTer
17 18 19 20 21 22 23 24 25 26 27 28 29 30 31 32

CCTTGCTCTGACTCCTTGCACTTCTGAGTGTTATACATACTTATTTTCATAGAGTCGGGACAAGAAAATGA terminator
AGTAAAAAAACGACGGGTGTGAAAGAGTTTATATTCACACCCGTTTTTATATTCGGCTTTAAGGAGGAACAC
AATTGTAGAACGGAAGAACCGGTTATTTTCGATCATGCGTTTTGAATAACATTCCAATAAAAATTCCAGTCT
CTTCCTCAAATGCAGACAAAGGATGAAGGACTTAAGGGTACTTACCAGGTTTTATGGTTAAGAATATTTCT
AAGAACATCATATTTTTTATTAGGAAATTAATAAATGAGATTGATCACTCTAGA
                                                  Xbal Mutagenic Oligonucleotides
BstEII - BstBI Fragment
  Isolated from plasmid pGHF374

BstBI - SmaI Fragment
    Eco RI    Bst BI
1  TGAATTCAGATTCGAAAATCACTCCGCAATGGAAAAGT  ——> Klenow
           Klenow <——  GGCGTTACCTTTTCACTTAGTGAAACATGTGGGCCCAACTTCGAAACCA 2
                         Glu              Xma I  Hind III
                         Ile              Sma I
                     GGCGTTACCTTTTCATAAAGTGAAACATGTGGGCCCAACTTCGAAACCA 2E41
                     GGCGTTACCTTTTCATAACGTGAAACATGTGGGCCCAACTTCGAAACCA 2E41
                         IleAla                                    DHA5A
```

FIG.6A

Smal - BstEII Fragment
                Xma I
    Eco RI      Sma I
3 AGAATTCACACCCGGGTGTGTAACTGGTGCATTGCAAACTTG   ——> PCR
                ACACATTGACCACGTAACGTTTGAACGAAGGAAGTTT————————
———CATGTGGTCCT/
                                        /AGTAAAACCA———
—————————AAACACACTAACTTGTAACTGCAAAATCTCTAAATA
        PCR <——    GAACATTGACGTTTTAGAGATTTATCCATTGGGGTTTCGAAAGTG 4
                                          Bst EII Hind III BstEII - Xbal Fragment
    Eco RI      Bst EII Sna BI
5 GGAATTCATAGGTAACC TACGTAGCATCACCTTGCTCTGACTCCTTGC   ——> PCR
                CGTAGTGGAACGAGACTGAGGAACGTGAAGA————————
CATTTTGGTAAT/
                                        /TCTAGA———
—————————ATATTTTTTATTAGGAAATTAATAAATGAGATTGATCAC
        PCR <——    CCTTTAATTATTTACTCTAACTAGTGAGATCTAACTTCGAAGACG 6
                                          Xba I  Hind III

FIG.6B 5,576,420

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 545 base pairs
        ( B ) TYPE: nucleic acid
        ( C ) STRANDEDNESS: unknown
        ( D ) TOPOLOGY: unknown ( i i ) MOLECULE TYPE: DNA (genomic)

( v i ) ORIGINAL SOURCE:
        ( A ) ORGANISM: Bacillus subtilis ( i x ) FEATURE:
        ( A ) NAME/KEY: CDS
        ( B ) LOCATION: 19..186

( i x ) FEATURE:
        ( A ) NAME/KEY: mat_peptide
        ( B ) LOCATION: 91..186

( i x ) FEATURE:
        ( A ) NAME/KEY: protein_bind
        ( B ) LOCATION: 9..15
        ( C ) IDENTIFICATION METHOD: experimental
        ( D ) OTHER INFORMATION: /function="restriction site"
            / bound_moiety="BstEII"
            / evidence=EXPERIMENTAL ( i x ) FEATURE:
        ( A ) NAME/KEY: protein_bind
        ( B ) LOCATION: 540..545
        ( C ) IDENTIFICATION METHOD: experimental
        ( D ) OTHER INFORMATION: /function="restriction site"
            / bound_moiety="XbaI"
            / evidence=EXPERIMENTAL ( x i ) SEQUENCE DESCRIPTION: SEQ ID NO:1:

| | | | | | | | | | | | | | | | | |
|---|---|---|---|---|---|---|---|---|---|---|---|---|---|---|---|---|
| TGAAAGGAGG | TCACCAAT | ATG | TCA | AAG | TTC | GAT | GAT | TTC | GAT | TTG | GAT | GTT | | | | 51 |
| | | Met -24 | Ser | Lys | Phe | Asp -20 | Asp | Phe | Asp | Leu | Asp -15 | Val | | | | |
| GTG | AAA | GTC | TCT | AAA | CAA | GAC | TCA | AAA | ATC | ACT | CCG | CAA | TGG | AAA | AGT | 99 |
| Val | Lys | Val | Ser -10 | Lys | Gln | Asp | Ser | Lys -5 | Ile | Thr | Pro | Gln | Trp 1 | Lys | Ser | |
| GAA | TCA | CTT | TGT | ACA | CCA | GGA | TGT | GTA | ACT | GGT | GCA | TTG | CAA | ACT | TGC | 147 |
| Glu | Ser 5 | Leu | Cys | Thr | Pro | Gly 10 | Cys | Val | Thr | Gly | Ala 15 | Leu | Gln | Thr | Cys | |
| TTC | CTT | CAA | ACA | CTA | ACT | TGT | AAC | TGC | AAA | ATC | TCT | AAA | TAAGTAAAAC | | | 196 |
| Phe | Leu | Gln | Thr | Leu | Thr | Cys | Asn | Cys | Lys | Ile 30 | Ser | Lys | | | | |
| 20 | | | | 25 | | | | | | | | | | | | |

| | | | | | |
|---|---|---|---|---|---|
| CATTAGCATC | ACCTTGCTCT | GACTCCTTGC | ACTTCTGAGT | GTTATACATA | CTTATTTTCA | 256 |
| TAGAGTCGGG | ACAAGAAAAT | GAAGTAAAAA | ACGACGGGTG | TGAAAGAGTT | TATATTCACA | 316 |
| CCCGTTTTTA | TATTCGGCTT | TAAGGAGGAA | CACAATTGTA | GAACGGAAGA | ACGGTTATTT | 376 |
| TCGATCATGC | GTTTTGAATA | ACATTCCAAT | AAAAATTCCA | GTCTCTTCCT | CAAATGCAGA | 436 |
| CAAAGGATGA | AGGACTTAAG | GGTACTTACC | AGGTTTTATG | GTTAAGAATA | TTTCTAAGAA | 496 |
| CATCATATTT | TTTATTAGGA | AATTAATAAA | TGAGATTGAT | CACTCTAGA | | 545 |

( 2 ) INFORMATION FOR SEQ ID NO:2:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | |
|---|---|---|---|---|---|---|---|---|---|---|---|---|---|
| Met -24 | Ser | Lys | Phe | Asp -20 | Asp | Phe | Asp | Leu | Asp -15 | Val | Val | Lys | Val | Ser | Lys -10 |
| Gln | Asp | Ser | Lys -5 | Ile | Thr | Pro | Gln | Trp 1 | Lys | Ser | Glu | Ser 5 | Leu | Cys | Thr |
| Pro | Gly 10 | Cys | Val | Thr | Gly | Ala 15 | Leu | Gln | Thr | Cys | Phe 20 | Leu | Gln | Thr | Leu |
| Thr 25 | Cys | Asn | Cys | Lys | Ile 30 | Ser | Lys | | | | | | | | |

( 2 ) INFORMATION FOR SEQ ID NO:3:

( i ) SEQUENCE CHARACTERISTICS:
        ( A ) LENGTH: 545 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: protein_bind
        ( B ) LOCATION: 9..15
        ( C ) IDENTIFICATION METHOD: experimental
        ( D ) OTHER INFORMATION: /function="restriction site"
            / bound_moiety="BstEII"
            / evidence=EXPERIMENTAL ( i x ) FEATURE:
        ( A ) NAME/KEY: protein_bind
        ( B ) LOCATION: 42..47
        ( D ) OTHER INFORMATION: /function="restriction site"
            / bound_moiety="Xba I"

( i x ) FEATURE:
        ( A ) NAME/KEY: protein_bind
        ( B ) LOCATION: 72..78

( D ) OTHER INFORMATION: /function="restriction site"
/ bound_moiety="Bst BI"

( i x ) FEATURE:
( A ) NAME/KEY: protein_bind
( B ) LOCATION: 115..120

( i x ) FEATURE:
( A ) NAME/KEY: protein_bind
( B ) LOCATION: 189..195

( i x ) FEATURE:
( A ) NAME/KEY: protein_bind
( B ) LOCATION: 196..201
( D ) OTHER INFORMATION: /function="restriction site"
/ bound_moiety="Sna BI"

( i x ) FEATURE:
( A ) NAME/KEY: protein_bind
( B ) LOCATION: 540..545
( D ) OTHER INFORMATION: /function="restriction site"
/ bound_moiety="XbaI"

( x i ) SEQUENCE DESCRIPTION: SEQ ID NO:3:

| | | | | | |
|---|---|---|---|---|---|
| TGAAAGGAGG | TCACCAATAT | GTCAAAGTTC | GATGATTTCG | ATCTAGATGT | TGTGAAAGTC | 60
| TCTAAACAAG | ATTCGAAAAT | CACTCCGCAA | TGGAAAAGTG | AATCACTTTG | TACACCCGGG | 120
| TGTGTAACTG | GTGCATTGCA | AACTTGCTTC | CTTCAAACAC | TAACTTGTAA | CTGCAAAATC | 180
| TCTAAATAGG | TAACCTACGT | AGCATCACCT | TGCTCTGACT | CCTTGCACTT | CTGAGTGTTA | 240
| TACATACTTA | TTTTCATAGA | GTCGGGACAA | GAAATGAAG | TAAAAAACGA | CGGGTGTGAA | 300
| AGAGTTTATA | TTCACACCCG | TTTTTATATT | CGGCTTTAAG | GAGGAACACA | ATTGTAGAAC | 360
| GGAAGAACGG | TTATTTTCGA | TCATGCGTTT | TGAATAACAT | TCCAATAAAA | ATTCCAGTCT | 420
| CTTCCTCAAA | TGCAGACAAA | GGATGAAGGA | CTTAAGGGTA | CTTACCAGGT | TTTATGGTTA | 480
| AGAATATTTC | TAAGAACATC | ATATTTTTA | TTAGGAAATT | AATAAATGAG | ATTGATCACT | 540
| CTAGA | | | | | | 545

( 2 ) INFORMATION FOR SEQ ID NO:4:

( i ) SEQUENCE CHARACTERISTICS:
( A ) LENGTH: 49 base pairs
( B ) TYPE: nucleic acid
( C ) STRANDEDNESS: unknown
( D ) TOPOLOGY: linear ( i i ) MOLECULE TYPE: DNA (genomic)

( v i ) ORIGINAL SOURCE:
( A ) ORGANISM: Bacillus subtilis ( x i ) SEQUENCE DESCRIPTION: SEQ ID NO:4:

GGCGTTACCT TTTCACTTAG TGAAACATGT GGGCCCAACT TCGAAACCA    49

( 2 ) INFORMATION FOR SEQ ID NO:5:

( i ) SEQUENCE CHARACTERISTICS:
( A ) LENGTH: 49 base pairs
( B ) TYPE: nucleic acid
( C ) STRANDEDNESS: unknown
( D ) TOPOLOGY: linear ( i i ) MOLECULE TYPE: DNA (genomic)

( x i ) SEQUENCE DESCRIPTION: SEQ ID NO:5:

GGCGTTACCT TTTCATAAAG TGAAACATGT GGGCCCAACT TCGAAACCA    49

( 2 ) INFORMATION FOR SEQ ID NO:6:

( i ) SEQUENCE CHARACTERISTICS:
    ( A ) LENGTH: 545 base pairs
    ( B ) TYPE: nucleic acid
    ( C ) STRANDEDNESS: unknown
    ( D ) TOPOLOGY: unknown ( i i ) MOLECULE TYPE: DNA (genomic)

( i x ) FEATURE:
    ( A ) NAME/KEY: CDS
    ( B ) LOCATION: 19..186

( i x ) FEATURE:
    ( A ) NAME/KEY: mat_peptide
    ( B ) LOCATION: 91..186

( i x ) FEATURE:
    ( A ) NAME/KEY: protein_bind
    ( B ) LOCATION: 9..15
    ( C ) IDENTIFICATION METHOD: experimental
    ( D ) OTHER INFORMATION: /function="restriction site"
        / bound_moiety="BstEII"
        / evidence=EXPERIMENTAL ( i x ) FEATURE:
    ( A ) NAME/KEY: protein_bind
    ( B ) LOCATION: 42..47
    ( D ) OTHER INFORMATION: /function="restriction site"
        / bound_moiety="Xba I"

( i x ) FEATURE:
    ( A ) NAME/KEY: protein_bind
    ( B ) LOCATION: 72..78
    ( D ) OTHER INFORMATION: /function="restriction site"
        / bound_moiety="Bst BI"

( i x ) FEATURE:
    ( A ) NAME/KEY: protein_bind
    ( B ) LOCATION: 115..120

( i x ) FEATURE:
    ( A ) NAME/KEY: protein_bind
    ( B ) LOCATION: 189..195

( i x ) FEATURE:
    ( A ) NAME/KEY: protein_bind
    ( B ) LOCATION: 196..201
    ( D ) OTHER INFORMATION: /function="restriction site"
        / bound_moiety="Sna BI"

( i x ) FEATURE:
    ( A ) NAME/KEY: protein_bind
    ( B ) LOCATION: 540..545
    ( D ) OTHER INFORMATION: /function="restriction site"
        / bound_moiety="XbaI"

( x i ) SEQUENCE DESCRIPTION: SEQ ID NO:6:

```
TGAAAGGAGG TCACCAAT ATG TCA AAG TTC GAT GAT TTC GAT CTA GAT GTT          51
                    Met Ser Lys Phe Asp Asp Phe Asp Leu Asp Val
                    -24             -20                 -15

GTG AAA GTC TCT AAA CAA GAT TCG AAA ATC ACT CCG CAA TGG AAA AGT          99
Val Lys Val Ser Lys Gln Asp Ser Lys Ile Thr Pro Gln Trp Lys Ser
            -10              -5                       1

ATT TCA CTT TGT ACA CCC GGG TGT GTA ACT GGT GCA TTG CAA ACT TGC         147
Ile Ser Leu Cys Thr Pro Gly Cys Val Thr Gly Ala Leu Gln Thr Cys
        5               10              15

TTC CTT CAA ACA CTA ACT TGT AAC TGC AAA ATC TCT AAA TAGGTAACCT          196
Phe Leu Gln Thr Leu Thr Cys Asn Cys Lys Ile Ser Lys
 20              25              30

ACGTAGCATC ACCTTGCTCT GACTCCTTGC ACTTCTGAGT GTTATACATA CTTATTTTCA       256

TAGAGTCGGG ACAAGAAAAT GAAGTAAAAA ACGACGGGTG TGAAAGAGTT TATATTCACA       316

CCCGTTTTTA TATTCGGCTT TAAGGAGGAA CACAATTGTA GAACGGAAGA ACGGTTATTT       376
```

```
TCGATCATGC GTTTTGAATA ACATTCCAAT AAAAATTCCA GTCTCTTCCT CAAATGCAGA      436

CAAAGGATGA AGGACTTAAG GGTACTTACC AGGTTTTATG GTTAAGAATA TTTCTAAGAA      496

CATCATATTT TTTATTAGGA AATTAATAAA TGAGATTGAT CACTCTAGA                  545
```

( 2 ) INFORMATION FOR SEQ ID NO:7:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Ser Lys Phe Asp Asp Phe Asp Leu Asp Val Val Lys Val Ser Lys
-24             -20                 -15                 -10

Gln Asp Ser Lys Ile Thr Pro Gln Trp Lys Ser Ile Ser Leu Cys Thr
             -5              1                   5

Pro Gly Cys Val Thr Gly Ala Leu Gln Thr Cys Phe Leu Gln Thr Leu
         10              15                  20

Thr Cys Asn Cys Lys Ile Ser Lys
 25              30
```

( 2 ) INFORMATION FOR SEQ ID NO:8:

( i ) SEQUENCE CHARACTERISTICS:
        ( A ) LENGTH: 545 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 19..186

( i x ) FEATURE:
        ( A ) NAME/KEY: mat_peptide
        ( B ) LOCATION: 91..186

( i x ) FEATURE:
        ( A ) NAME/KEY: protein_bind
        ( B ) LOCATION: 9..15
        ( C ) IDENTIFICATION METHOD: experimental
        ( D ) OTHER INFORMATION: /function="restriction site"
            / bound_moiety="BstEII"
            / evidence=EXPERIMENTAL ( i x ) FEATURE:
        ( A ) NAME/KEY: protein_bind
        ( B ) LOCATION: 42..47
        ( D ) OTHER INFORMATION: /function="restriction site"
            / bound_moiety="Xba I"

( i x ) FEATURE:
        ( A ) NAME/KEY: protein_bind
        ( B ) LOCATION: 72..78
        ( D ) OTHER INFORMATION: /function="restriction site"
            / bound_moiety="Bst BI"

( i x ) FEATURE:
        ( A ) NAME/KEY: protein_bind
        ( B ) LOCATION: 115..120

( i x ) FEATURE:
        ( A ) NAME/KEY: protein_bind
        ( B ) LOCATION: 189..195

( i x ) FEATURE:
        ( A ) NAME/KEY: protein_bind

-continued ( B ) LOCATION: 196..201
          ( D ) OTHER INFORMATION: /function="restriction site"
                  / bound_moiety="Sna BI"

( i x ) FEATURE:
          ( A ) NAME/KEY: protein_bind
          ( B ) LOCATION: 540..545
          ( D ) OTHER INFORMATION: /function="restriction site"
                  / bound_moiety="XbaI"

( x i ) SEQUENCE DESCRIPTION: SEQ ID NO:8:

| TGAAAGGAGG | TCACCAAT | ATG | TCA | AAG | TTC | GAT | GAT | TTC | GAT | CTA | GAT | GTT | 51 |
|   |   | Met | Ser | Lys | Phe | Asp | Asp | Phe | Asp | Leu | Asp | Val |   |
|   |   | -24 |   |   |   | -20 |   |   |   |   | -15 |   |   |

| GTG | AAA | GTC | TCT | AAA | CAA | GAT | TCG | AAA | ATC | ACT | CCG | CAA | TGG | AAA | AGT | 99 |
| Val | Lys | Val | Ser | Lys | Gln | Asp | Ser | Lys | Ile | Thr | Pro | Gln | Trp | Lys | Ser |   |
|   |   |   | -10 |   |   |   |   | -5 |   |   |   |   | 1 |   |   |   |

| ATT | GCA | CTT | TGT | ACA | CCC | GGG | TGT | GTA | ACT | GGT | GCA | TTG | CAA | ACT | TGC | 147 |
| Ile | Ala | Leu | Cys | Thr | Pro | Gly | Cys | Val | Thr | Gly | Ala | Leu | Gln | Thr | Cys |   |
|   | 5 |   |   |   |   | 10 |   |   |   |   | 15 |   |   |   |   |   |

| TTC | CTT | CAA | ACA | CTA | ACT | TGT | AAC | TGC | AAA | ATC | TCT | AAA | TAGGTAACCT | 196 |
| Phe | Leu | Gln | Thr | Leu | Thr | Cys | Asn | Cys | Lys | Ile | Ser | Lys |   |   |
| 20 |   |   |   |   | 25 |   |   |   |   | 30 |   |   |   |   |

| ACGTAGCATC | ACCTTGCTCT | GACTCCTTGC | ACTTCTGAGT | GTTATACATA | CTTATTTTCA | 256 |
| TAGAGTCGGG | ACAAGAAAAT | GAAGTAAAAA | ACGACGGGTG | TGAAAGAGTT | TATATTCACA | 316 |
| CCCGTTTTTA | TATTCGGCTT | TAAGGAGGAA | CACAATTGTA | GAACGGAAGA | ACGGTTATTT | 376 |
| TCGATCATGC | GTTTTGAATA | ACATTCCAAT | AAAAATTCCA | GTCTCTTCCT | CAAATGCAGA | 436 |
| CAAAGGATGA | AGGACTTAAG | GGTACTTACC | AGGTTTTATG | GTTAAGAATA | TTTCTAAGAA | 496 |
| CATCATATTT | TTTATTAGGA | AATTAATAAA | TGAGATTGAT | CACTCTAGA |   | 545 |

( 2 ) INFORMATION FOR SEQ ID NO:9:

( i ) SEQUENCE CHARACTERISTICS:
          ( A ) LENGTH: 56 amino acids
          ( B ) TYPE: amino acid
          ( D ) TOPOLOGY: linear ( i i ) MOLECULE TYPE: protein ( x i ) SEQUENCE DESCRIPTION: SEQ ID NO:9:

| Met | Ser | Lys | Phe | Asp | Asp | Phe | Asp | Leu | Asp | Val | Val | Lys | Val | Ser | Lys |
| -24 |   |   |   | -20 |   |   |   | -15 |   |   |   |   |   | -10 |   |

| Gln | Asp | Ser | Lys | Ile | Thr | Pro | Gln | Trp | Lys | Ser | Ile | Ala | Leu | Cys | Thr |
|   |   |   | -5 |   |   |   |   | 1 |   |   |   |   | 5 |   |   |

| Pro | Gly | Cys | Val | Thr | Gly | Ala | Leu | Gln | Thr | Cys | Phe | Leu | Gln | Thr | Leu |
|   |   | 10 |   |   |   |   | 15 |   |   |   |   | 20 |   |   |   |

| Thr | Cys | Asn | Cys | Lys | Ile | Ser | Lys |
|   | 25 |   |   |   | 30 |   |   |

( 2 ) INFORMATION FOR SEQ ID NO:10:

( i ) SEQUENCE CHARACTERISTICS:
          ( A ) LENGTH: 51 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:10:

GGCGTTACCT TTTCATAACG TGTGAAACAT GTGGGCCCAA CTTCGAAACC A          51

( 2 ) INFORMATION FOR SEQ ID NO:11:

( i ) SEQUENCE CHARACTERISTICS:
        ( A ) LENGTH: 38 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:11:

TGAATTCAGA TTCGAAAATC ACTCCGCAAT GGAAAAGT        38

( 2 ) INFORMATION FOR SEQ ID NO:12:

( i ) SEQUENCE CHARACTERISTICS:
        ( A ) LENGTH: 42 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:12:

AGAATTCACA CCCGGGTGTG TAACTGGTGC ATTGCAAACT TG        42

( 2 ) INFORMATION FOR SEQ ID NO:13:

( i ) SEQUENCE CHARACTERISTICS:
        ( A ) LENGTH: 11 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:13:

CATGTGGTCC T        11

( 2 ) INFORMATION FOR SEQ ID NO:14:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:14:

ACACATTGAC CACGTAACGT TTGAACGAAG GAAGTTT        37

( 2 ) INFORMATION FOR SEQ ID NO:15:

( i ) SEQUENCE CHARACTERISTICS:
        ( A ) LENGTH: 36 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:15:

AAACACACTA ACTTGTAACT GCAAAATCTC TAAATA        36

( 2 ) INFORMATION FOR SEQ ID NO:16:

( i ) SEQUENCE CHARACTERISTICS:
        ( A ) LENGTH: 10 base pairs
        ( B ) TYPE: nucleic acid ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:16:

AGTAAAACCA  10

( 2 ) INFORMATION FOR SEQ ID NO:17:

( i ) SEQUENCE CHARACTERISTICS:
        ( A ) LENGTH: 45 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:17:

GAACATTGAC GTTTTAGAGA TTTATCCATT GGGGTTTCGA AAGTG  45

( 2 ) INFORMATION FOR SEQ ID NO:18:

( i ) SEQUENCE CHARACTERISTICS:
        ( A ) LENGTH: 47 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:18:

GGAATCATAG GTAACCTACG TAGCATCACC TTGCTCTGAC TCCTTGC  47

( 2 ) INFORMATION FOR SEQ ID NO:19:

( i ) SEQUENCE CHARACTERISTICS:
        ( A ) LENGTH: 12 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:19:

CATTTTGGTA AT  12

( 2 ) INFORMATION FOR SEQ ID NO:20:

( i ) SEQUENCE CHARACTERISTICS:
        ( A ) LENGTH: 31 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:20:

CGTAGTGGAA CGAGACTGAG GAACGTGAAG A  31

( 2 ) INFORMATION FOR SEQ ID NO:21:

( i ) SEQUENCE CHARACTERISTICS:
        ( A ) LENGTH: 39 base pairs
        ( B ) TYPE: nucleic acid
        ( C ) STRANDEDNESS: unknown
        ( D ) TOPOLOGY: linear ( i i ) MOLECULE TYPE: DNA (genomic)

-continued ( x i ) SEQUENCE DESCRIPTION: SEQ ID NO:21:

ATATTTTTA TTAGGAAATT AATAAATGAG ATTGATCAC  39

( 2 ) INFORMATION FOR SEQ ID NO:22:

( i ) SEQUENCE CHARACTERISTICS:
        ( A ) LENGTH: 45 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:22:

CCTTTAATTA TTTACTCTAA CTAGTGAGAT CTAACTTCGA AGACG  45

( 2 ) INFORMATION FOR SEQ ID NO:23:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

Trp Lys Ser Ile Ser Leu Cys Thr Pro Gly Cys Val Thr Gly Ala Leu
 1               5                  10                 15

Gln Thr Cys Phe Leu Gln Thr Leu Thr Cys Asn Cys Lys Ile Ser Lys
            20                  25                  30

( 2 ) INFORMATION FOR SEQ ID NO:24:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

Trp Lys Ser Ile Ala Leu Cys Thr Pro Gly Cys Val Thr Gly Ala Leu
 1               5                  10                 15

Gln Thr Cys Phe Leu Gln Thr Leu Thr Cys Asn Cys Lys Ile Ser Lys
            20                  25                  30

SUBTILIN VARIANT OF ENHANCED STABILITY AND ACTIVITY

This is a division of Ser. No. 07/981,525, filed Nov. 25, 1992, now U.S. Pat. No. 5,516,682, which is a continuation-in-part of Ser. No. 07/214,959, filed Jul. 5, 1988, now U.S. Pat. No. 5,218,101.

FIELD OF THE INVENTION

This invention pertains to a method of converting non-bacteriocin expressing Bacillus strains to bacteriocin expressing Bacillus strain, and to mutant form of subtilin produced by that method. Specifically, a form of subtilin having enhanced stability and activity as addressed, together with the gene therefore, and expression vehicles for that gene.

BACKGROUND OF THE PRIOR ART

In parent application Ser. No. 07/214,959, the polypeptide precursors for expression of mature subtilin and nisin, and corresponding gene sequences, are disclosed. As related in the parent application, these bacteriocins are of particular interest in that they contain unusual amino acids that are introduced subsequent to nucleic acid translation, presumably by specific enzyme mechanisms contained within the cell, and possibly on the ribosome. Thus, the parent application identifies the gene and amino acid leader sequence necessary for the expression of the polypeptide precursor which, upon undergoing posttranslational modification, results in the expression of the mature bacteriocin.

While these two antibiotics share considerable structural homology, as discussed in the parent application, they are quite distinct in certain chemical properties. Of particular importance is tendency of the subtilins to undergo spontaneous inactivation at a substantially greater rate than that exhibited by nisin. In aqueous solution at pH 6.8, spontaneous inactivation is accompanied by chemical modification of the dehydroalanine at position 5 of the mature bacteriocin, with a kinetic first-order $t_{1/2}$ of 0.8 days. It is noted that the amino acid in the four position, Glu, bares a R-group on its carboxyl moiety, which may participate in the chemical modification of the adjacent amino acid residue.

Thus, nisin, which is resistant to inactivation at low pH and high temperatures, Hurst, *Advanced Application of Microbiology*, volume 27, pages 85–123 (1981) is widely used as a food preservative, Hurst, supra as well as Jay, *Food Microbiology*, vol. 8, pages 117–143 (1983) and a treatment for bacterial infections, Sears et al, *Journal of Diary Science* 74, page 203 (1991). In contrast, subtilin's instability renders it of little practical value, despite having a broad spectrum of action. Jay, Supra.

It is clearly a desire of those of skill in the art to obtain a mature form of subtilin which is resistant to inactivation and exhibits reasonable activity, to provide an antibiotic with the potential utility of nisin. This is particularly important in light of the increasing antibiotic resistance observed among microbial populations due to the widespread use of existing antibiotics. It is further desirable of producing subtilin forms from a *Bacillus* host to obtain improvements in yield, and take advantage of developments.

SUMMARY OF THE INVENTION

A mutant subtilin of enhanced stability and increased specific activity has the amino acid sequence of native mature subtilin, saved for the substitution, at the four position, of isoleucine for the glutamate of native, naturally occurring subtilin. This substitution results in a 57-fold increase in chemical and biological stability, as well as a 3–4 fold increase in specific activity. Apparently, the glutamate carboxyl moiety participates in the chemical modification of the dehydroalanine at position 5, but the isoleucine does not induce that modification, thus enhancing the stability of the dehydroalanine moiety at position 5. The three to four-fold increase is totally unpredicted.

Figure 3:
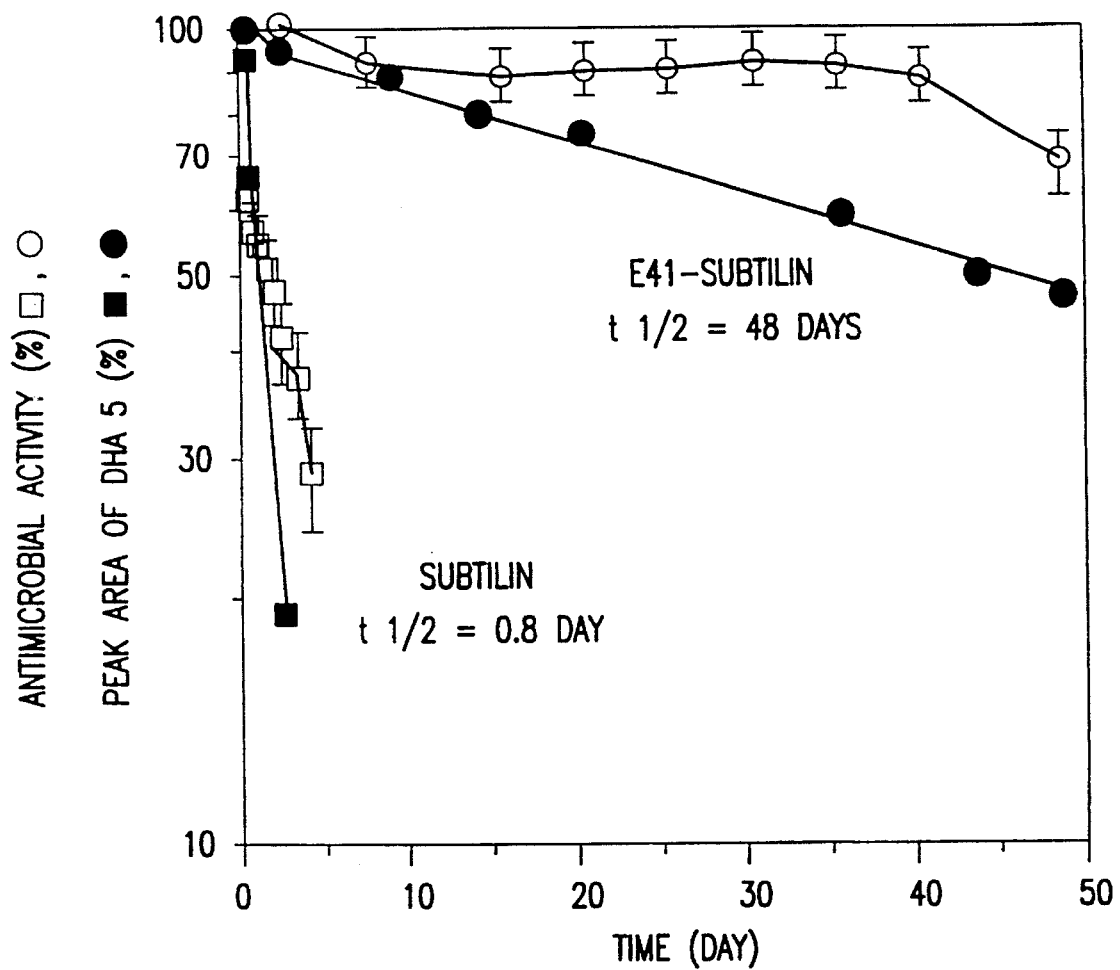

The graph of FIG. 3 compares the disappearance of the $DHI_5$ resonance peak and proton NMR spectra of natural subtilin and the E4I-subtilin mutant.

Figure 4:
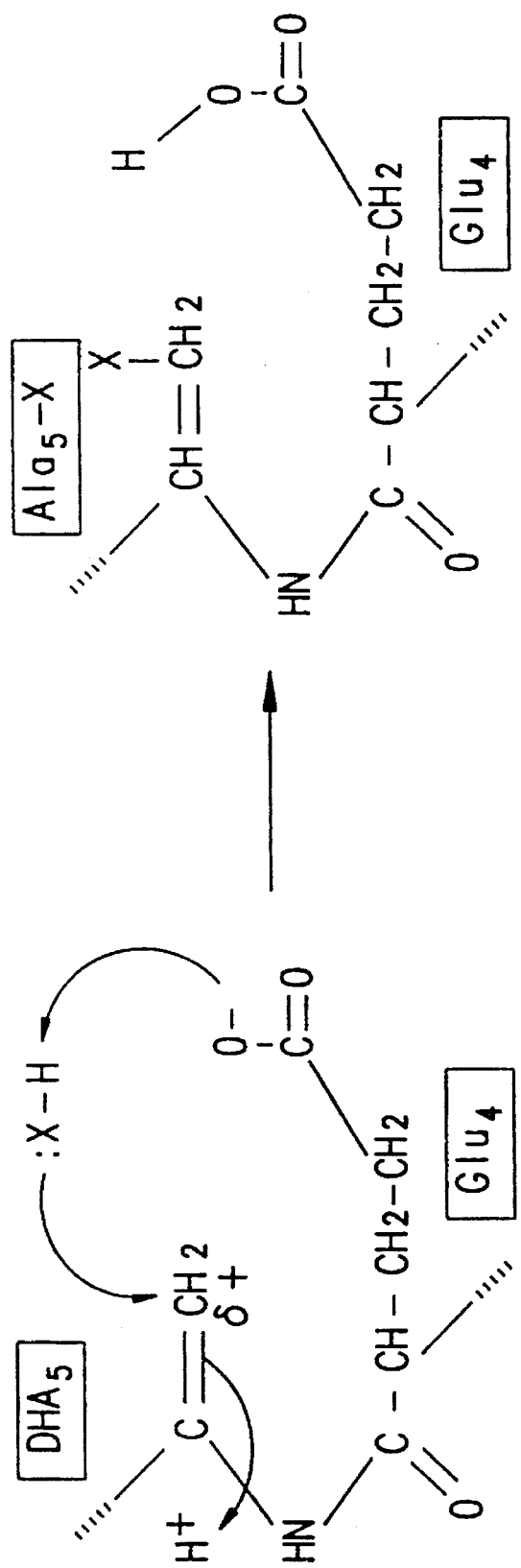

FIG. 4 illustrates a hypothetical mechanism for the modification of the $DHA_5$ residue of subtilin as assisted by the carboxyl moiety of the $Glu_4$ residue of native subtilin.

FIG. 5A–E is an illustration of the spa operon in the host-vector pair used for mutagenesis and replacement of the chromosomal subtilin gene with the mutant subtilin gene.

FIG. 6 is an illustration of the mutagenesis of the BstEII-XbaI restriction fragment employed in the claimed invention. The wild-type sequence (SEQ ID NO:1) contains the subtilin structural gene. The nucleotide changes, shown above the sequence along with the name of the resulting restriction site (SEQ ID NO:3), are made of silent codons that do not alter the translation product of the gene.

Figure 7:
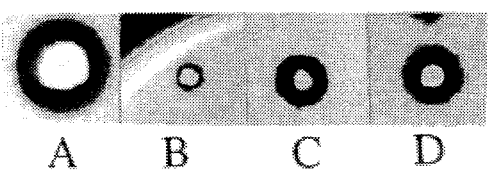

FIG. 7 is an illustration of a representative halo assay of colonies producing both subtilin and the E4I-subtilin mutant.

DETAILED DESCRIPTION OF THE INVENTION

Native subtilin exhibits a dehydroalanine moiety at the 5 position ($DHA_5$). As inactivation of subtilin induced by chemical or biological environments is accompanied by modification of the $DHA_5$ moiety, with a kinetic first-order of $p_{1/2}$ of 0.8 days, this modification is believed to correspond to the loss of activity in subtilin. As illustrated in FIG. 4, this chemical modification of $DHA_5$ is believed assisted by the carboxyl moiety of the amino acid residue of the 4 position $Glu_4$.

Not withstanding the susceptibility of $DHA_5$ to chemical inactivation, replacement of $DHA_5$ with the corresponding amino acid alanine (retaining the hydrophobicity of the native residue while destroying the double bond) resulted in a complete loss of activity against bacterial spore outgrowth. Thus, maintenance of the $DHA_5$ moiety is a prerequisite to maintaining activity.

As the glutamate of amino acid residue 4 is suspected of contributing to the inactivation of native subtilin, this moiety was converted, by site-specific mutagenesis, to isoleucine. The $DHA_5$ of this mutant subtilin, designated E4I-subtilin, underwent chemical modification with a $t_{1/2}$ of 48 days, 57-fold slower than native subtilin. As illustrated in FIG. 3, the rate of loss of biological activity dropped by a similar amount.

Totally unpredicted, the specific activity of E4I-subtilin was 3–4 fold higher than natural subtilin.

The site-specific mutagenesis required to convert native subtilin to E4I subtilin, the isolation of the same, monitoring of $DHI_5$ utility and measure of biological stability, are all detailed in the following specific examples.

Bacterial strains, cloning vectors, and culture conditions. Cloning in *Escherichia coli* was carried out by standard procedures, Maniatis et al, *Molecular Cloning: A Laboratory Manual* (1982). Transformations of competent *Bacillus subtilis* cells were performed as described, Wilson et al, *J. Bacteriol.*, 94, 562–570 and 95, 1439–1449 (1967 and 1968) as well as Young et al, *Handbook of Genetics*, Vol. 1, pp. 69–114 (1974). PAB medium is Antibiotic Medium 3 (Difco), and TBAB medium is Tryptose Blood Agar Base (Difco); plates contained 0.8% agar. Chloramphenicol and erythromycin (Sigma) were employed at 10 μg per mL.

Isolation of natural and mutant subtilin. Natural subtilin was isolated from *B. subtilis* ATCC 6633 culture supernatants by a modification of previously published procedures, Jensen and Hirschman, *Arch. Biochem.*, 4, 197–309 (1944). Cells were grown in Medium A, Bannerjee and Hansen, *J. Biol. Chem.*, 263, 9508–9514 (1988), containing 10% sucrose and incubated with good aeration for 30–35 hours at 35° C. The culture was acidified to pH 2.8 with phosphoric acid and heated in an autoclave at 121° C. for 3 min to inactivate proteases, and cooled to room temp. One-half vol of n-butanol was added, stirred at 4° C. for 2 hours, allowed to stand at 4° C. for 2 hours, and centrifuged. 2.5 volume of acetone were added to the supernatant, allowed to stand at −20° C. for at least 2 hours, and centrifuged. Most of the pellet is subtilin, which was washed with 95% ethanol, briefly lyophilized, and dissolved in 0.1% trifluoroacetic acid. This was immediately purified by RP-HPLC as described previously for nisin (20), which employed a trifluoroacetic acid-water-acetonitrile gradient. Subtilin elutes slightly later than nisin in this gradient. Peaks were collected, lyophilized, and stored at −80° C. Subtilin that was to be subjected to proton NMR spectral analysis was dissolved in deuterated water (99.96 atom % D, Aldrich Chemical Co.) and lyophilized (repeated twice) to exchange protons. The E4I-subtilin mutant was isolated in the same way, except that the cells were crown in Medium A with 2% sucrose, and the E4I-subtilin eluted somewhat later in the HPLC gradient than natural subtilin, which reflected the fact that E4I-subtilin is slightly more hydrophobic than subtilin. It has been reported that subtilin is light-sensitive (1), so subtilin and E4I-subtilin samples were routinely protected from light. Whether E4I-subtilin is light-sensitive was not determined.

Amino acid composition analysis was performed with a Hewlett Packard (Fort Collins, Colo.) AminoQuant amino acid analyzer after HCl hydrolysis. N-terminal sequence analysis was performed on an Applied Biosystems (Foster City, Calif.) Model 477A peptide sequencer and Model 120A analyzer. Oligonucleotides were synthesized on a Biosearch Model 8500 oligonucleotide synthesizer.

Measurement of chemical stability of $DHA_5$. The dehydro residues of nisin and subtilin have vinyl protons that give well-separated resonances in the proton NMR spectrum, Liu and Hansen, *Appl. Environ. Microbiol.*, 56, 251–2558 (1990). The areas of the vinyl proton peaks in the NMR spectrum were measured, and chemical modification of $DHA_5$ over time was taken as the decrease in peak area of the $DHA_5$ vinyl protons in subtilin and in E4I-subtilin as compared to zero time. Proton NMR spectra were obtained using a Bruker AMX-500 NMR spectrometer. The spectra were obtained at a constant temperature of 295 K., using selective solvent suppression.

Measurement Of biological stability of subtilin. Biological activity was measured by a liquid assay in which various concentrations of subtilin were added to a suspension of *Bacillus cereus* T spores in 15 ml polypropylene tubes, and inhibitory effects were evaluated by phase-contrast microscopy as described previously (Morris et al, *J. Biol. Chem.*, 259, 13590–13594 (1984) and *Appl. Environ. Microbiol.*, 42, 958–962 (1981). The amount of subtilin required to inhibit spore outgrowth during the 3 hour assay period was used as a measure of antimicrobial activity. Relative amounts of subtilin were estimated from the area of the subtilin peak, (measured at 254 nm) that eluted from the C-18 analytical HPLC column during purification. The amounts were converted to molar quantities of subtilin by comparing the peak area of subtilin with that of a known molar quantity of a nisin standard (21). For this purpose, the extinction coefficients of nisin and subtilin at 254 nm were assumed to be the same, in that absorbance at this wavelength is mainly due to the same three dehydro residues present in both peptides. The biological activity of the E4I-subtilin mutant was determined in the same way as for natural subtilin.

Figure 1:
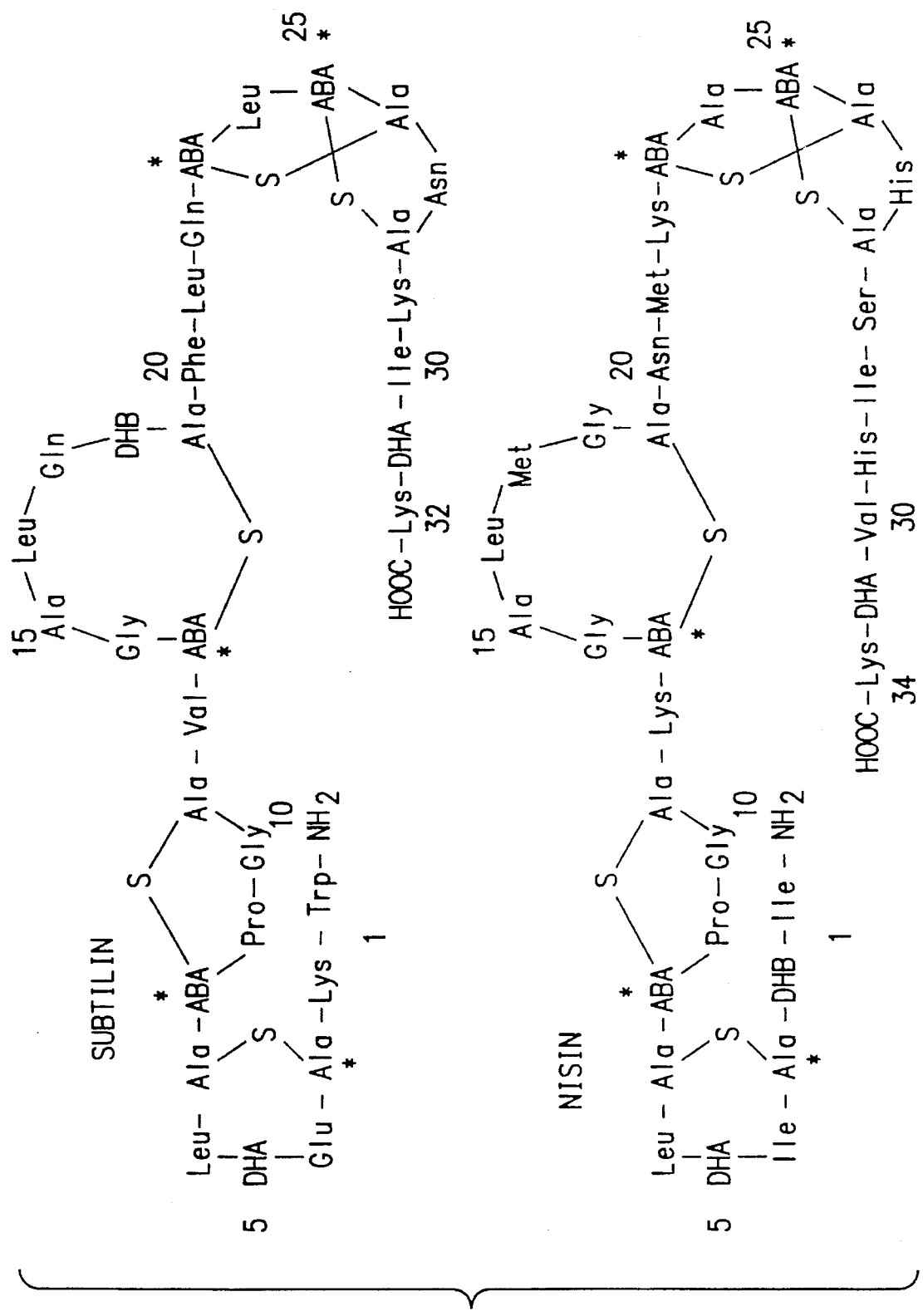
FIG. 1 is an illustration of the amino acid sequences for the bacteriocins subtilin and nisin. Asterisks indicate the amino acid has the (D)-stereo configuration at the α-carbon.
Figure 2A:
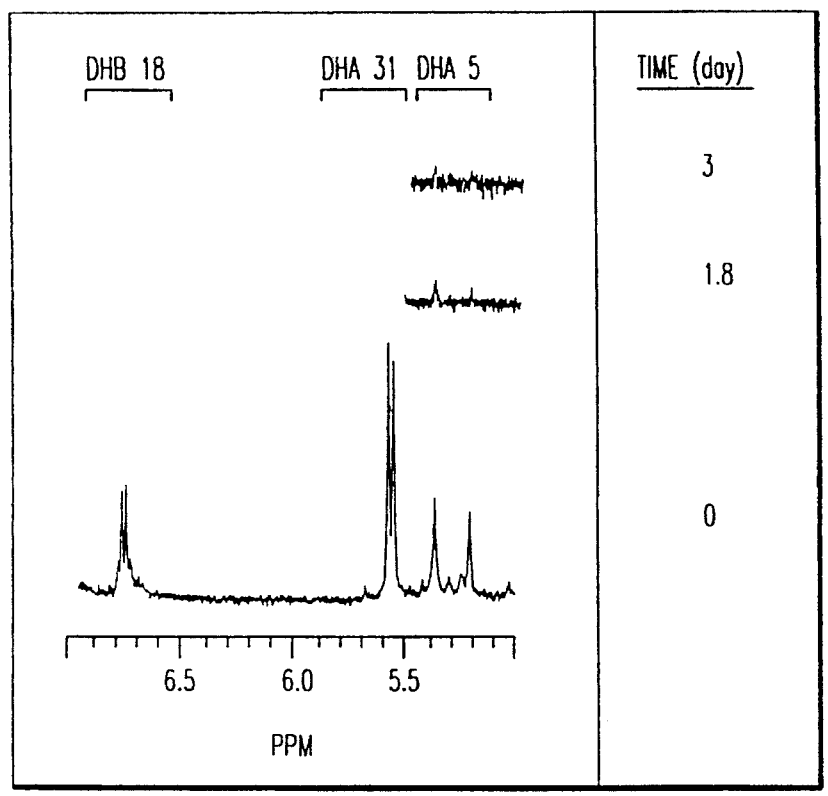
FIG. 2A and 2B are comparative proton NMR spectra of native subtilin and E4I-subtilin, the mutant of the claimed invention.
Figure 2B:
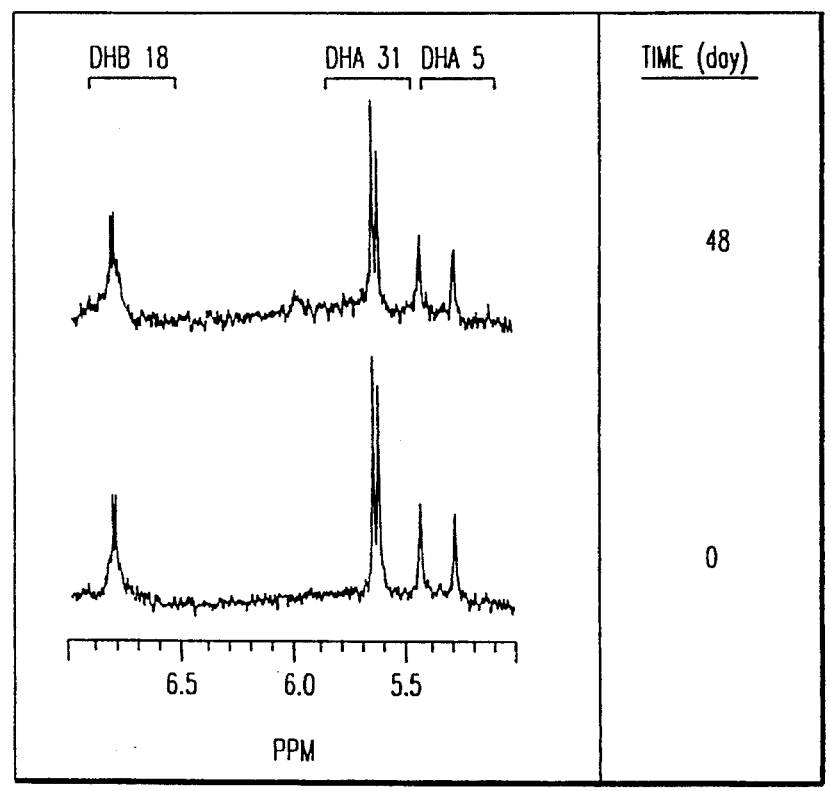

Chemical and biological stability of natural subtilin. The natural producer of subtilin is *B. subtilis* ATCC 6633. Subtilin was isolated and purified from a culture supernatant of this organism as described above. The purified subtilin was split into two samples, one of which was dissolved in $D_2O$ at pH 6.8 and subjected to proton NMR spectroscopy; and the other was dissolved in 50 mM NaPi at pH 6.8 and a portion assayed for biological activity. These dissolved samples were incubated at room temperature, and from time to time, the NMR spectrum of the one sample and the biological activity of the other sample were determined. The only vinyl proton peaks in the NMR spectrum that changed during incubation were those corresponding to $DHA_5$, which decreased in area over time (FIG. 2). FIG. 3 shows that the rate of disappearance of $DHA_5$ conforms to a first-order process with a $t_{1/2}$ of 0.8 days. FIG. 3 also shows that the biological activity dropped at approximately this same rate.

Although the chemical environment of $DHA_5$ that is responsible for its reactivity could be exerted from anywhere within the peptide, it is likely that residues in the immediate vicinity of $DHA_5$ are particularly important. This focuses attention on the three residues in the vicinity of $DHA_5$ that are different. Focusing still further, the glutamate residue at position 4, which is immediately adjacent to $DHA_5$, is particularly suspicious in that a mechanism by which it could participate in the modification of $DHA_5$ exists. One possibility is that the glutamate carboxyl could directly add to the double bond of $DHA_5$. Another, perhaps more likely, mechanism is that the glutamate carboxyl could act as a general base to activate a potential nucleophile by deprotonation as shown in FIG. 4. For example, if the nucleophile were a hydroxyl ion derived by deprotonation of a water molecule, one would expect to see a first-order modification rate of $DHA_5$, as was actually observed.

Figure 5:
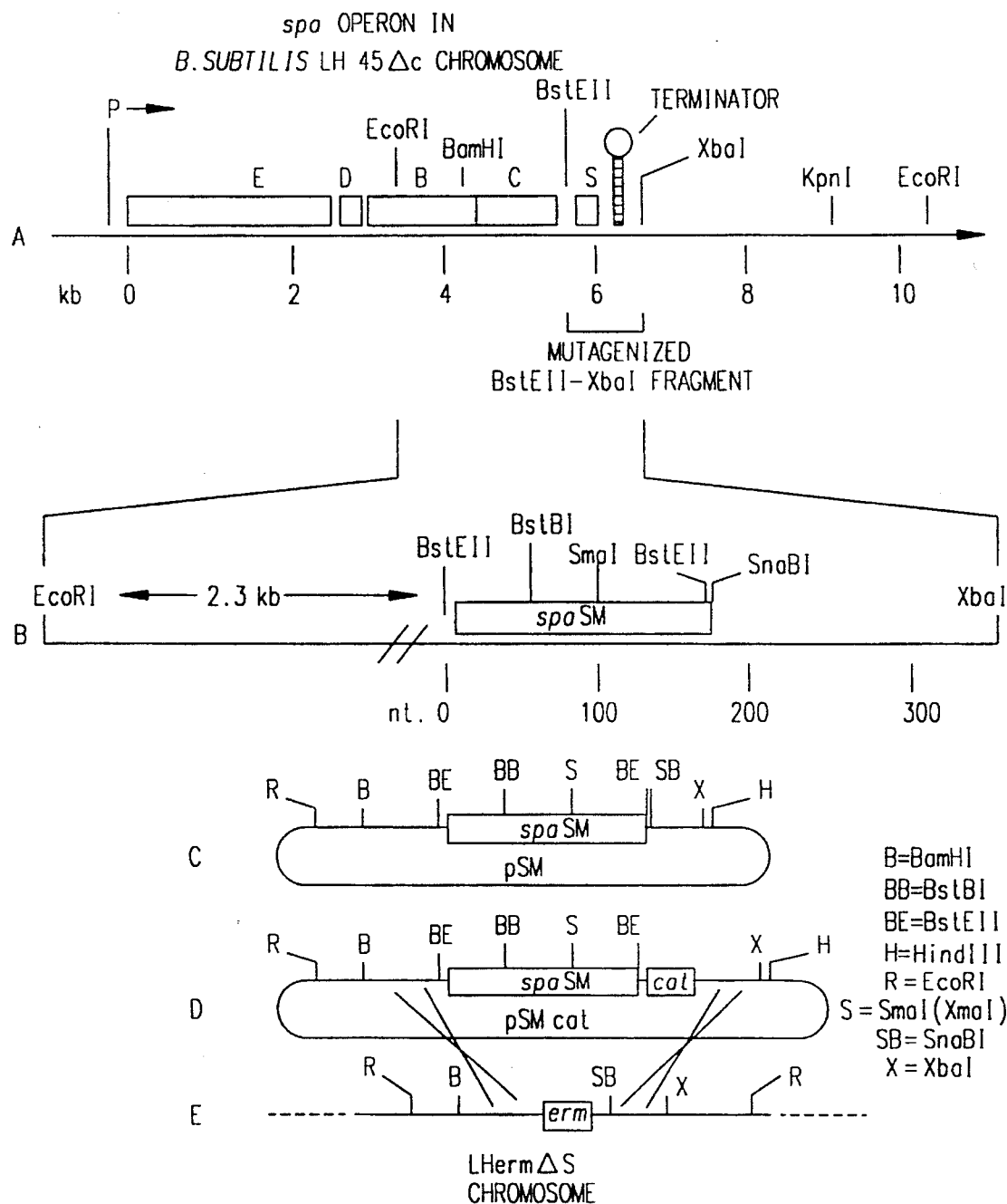

A host-vector system for mutagenesis of the subtilin gene. Mutagenesis of the subtilin gene required the development of a suitable host-vector system. The gene (spaS) that encodes the subtilin prepeptide is part of the spa operon in the chromosome of *Bacillus subtilis* (FIG. 5). It lies on a natural BstEII-XbaI restriction fragment whose sequence is shown in FIG. 6. The prepeptide gene is so small that it does not contain many useful restriction sites, so a sequence was engineered with changes at silent sites that would introduce new restriction sites without changing the translation product. The engineered sequence (SEQ ID NO:3) and the restriction sites introduced are shown in FIG. 6. The addition of these new restriction sites permits a cartridge mutagenesis approach to making mutations in the subtilin gene.

Previous attempts to express the subtilin prepeptide from a multi-copy plasmid in *Bacillus subtilis* failed, and it was concluded that mutants of the subtilin gene should be expressed by placing them in the chromosome at the site of the natural gene. If this were done by removing the natural gene before replacing it with the mutant copy, one would eliminate concern about ambiguities arising from simultaneous expression of natural and mutant copies within the same cell. The process of replacing chromosomal genes in *Bacillus subtilis* by a double-crossover between a linear plasmid and chromosomal sequences is well-established, requiring only that the plasmid contain a suitable selective marker flanked by appropriate chromosomal homologies. To achieve this, an erythromycin resistance (erm) gene was used to first replace, and thus delete, the natural chromosomal subtilin gene. The erm gene was then replaced by a mutant copy of the subtilin gene using a flanking chloramphenicol resistance (cat) gene as a selective marker, as illustrated in FIG. 5. The *B. subtilis* host cell (called LHermΔS) that contains the erm gene in place of the subtilin gene is also shown in FIG. 5. This LHermΔS-pSMcat host-vector pair has proved very versatile, and can be used to mutagenize the subtilin gene by a variety of site-directed and random strategies.

Prior to constructing a subtilin mutant, this system was tested thoroughly. The LHermΔS host, in which the natural subtilin gene had been replaced by an erm gene, was checked carefully to verify that it had erythromycin resistance, lacked the subtilin gene, and was unable to produce subtilin as established by a halo assay (FIG. 7). The engineered sequence in the pSMcat plasmid was confirmed by DNA sequence analysis, and then linearized and integrated into the LHermΔS host chromosome by a double-crossover, whereupon the host became erythromycin-sensitive and chloramphenicol-resistant, showing that replacement of the erm gene by the SMcat sequence had occurred. These cells produced normal amounts of subtilin activity (FIG. 7), showing that the silent mutations introduced into the sequence to give new restriction sites were indeed silent, and that transcription-translation of the gene was occurring normally. Southern hybridization analysis was used to show that the gene had integrated at the proper location in the chromosome.

Construction of E4I-subtilin. The E4I mutation was then introduced into the pSMcat plasmid by excising the BstBI-SmaI fragment (SEQ ID NO:4) and replacing it with the BstBI-SmaI mutagenic fragment (SEQ ID NO:5) to give plasmid pE4IScat, in which the Glu$_4$ codon had been replaced by an Ile codon. The fragment replacement was confirmed by DNA sequence analysis of the insert in pE4IScat. The mutagenized sequence (SEQ ID NO:6) was then introduced into the LHermΔS host chromosome by linearizing pE4IScat, transforming it into the host, and selecting for the double-crossover replacements on chloramphenicol-PAB plates. Chloramphenicol-resistant and erythromycin-sensitive colonies were found, showing that replacement of the erm gene with the mutant subtilin gene had occurred. Several chloramphenicol-resistant colonies were selected and subjected to Southern hybridization analysis to show that the mutant subtilin gene had been integrated into the LHermΔS host. One of these colonies, called LHE4IScat, was analyzed for subtilin-like activity in a halo assay, as shown in FIG. 7. The LHE4Icat colony produced a halo, showing that the E4I-subtilin that it produces has antimicrobial activity. This colony was grown up in culture, from which the putative E4I-subtilin (SEQ ID NO:7)was isolated and then purified by HPLC chromatography. The E4I-subtilin eluted later in the gradient, at higher concentrations of acetonitrile, than natural subtilin; which is consistent with the mutant being more hydrophobic, as would be expected. The E4I-subtilin was subjected to amino acid composition and N-terminal sequence analysis. The composition showed one more Ile and one less Glu (determined as Glx) than natural subtilin, as expected; but was otherwise identical to natural subtilin, as expected. The N-terminal sequence was Trp-Lys-(blank)-Ile(sequence blank from here on); compared to natural subtilin which gave Trp-Lys-(blank)Glu-(sequence blank from here on). The blank at residue 3 is expected, because the Ala remains tethered to the thioether group and is not released, Kellner et al, *Eur. J. Biochem.*, 177, 53–59 (1988) and Agnew, *Chem. Int. Ed. Engl.*, 28, 616–619 (1988), and the Edman degradation stops at residue 5 because it is unable to process a dehydro reside, Liu and Hansen, *J. Bacteriol.*, 173, 7387–7390 (1991). The composition analysis and N-terminal sequence thus show that the E4I-subtilin prepeptide has undergone the full complement of post-translational modifications, including dehydration of all serines and all threonines, formation of all thioether cross-linkages within the structural region, and accurate removal of the leader peptide. If even one of the several dehydrations or cross-linkages had not occurred, or if the leader sequence had been inaccurately cleaved, it would have been reflected as abnormal amino acid composition, or abnormal N-terminal sequence, or both.

E4I-subtilin has enhanced specific activity. The specific activity of E4I-subtilin was measured using the spore outgrowth assay and compared to natural subtilin. E4I-subtilin showed inhibition at about 0.3 μg per ml (80 nM), whereas normal subtilin showed inhibition at about 1 μg per ml (280 nM). The mutant subtilin was accordingly 3–4 times more potent than natural subtilin in this particular biological assay. It is worth noting that natural subtilin, and especially the mutant subtilin, are effective at molar concentrations that are appreciably lower (an order of magnitude) than other common antibiotics such as ampicillin or chloramphenicol.

E4I-subtilin has enhanced chemical and biological stability. The central design strategy in the construction of a stable mutant of subtilin was based on the idea that the chemical and biological stabilities of subtilin are determined by the chemical reactivity of DHA$_5$; and that DHA$_5$ in natural subtilin is unstable because the Glu$_4$ carboxyl participates in its chemical modification (FIG. 4). This idea led to a prediction that mutation of Glu$_4$ to Ile would enhance the chemical and biological stability of subtilin because the possibility of carboxyl-group participation in the modification of DHA$_5$ would be eliminated. The chemical stability of DHA$_5$ in E4I-subtilin was accordingly evaluated by observing the disappearance over time of the DHA$_5$ vinyl proton resonance peaks in the NMR spectra, as was done for natural subtilin. FIG. 3 shows that the rate of disappearance of DHA$_5$ conforms to a first-order rate process with a t$_{1/2}$ of 48 days. This is a dramatic 57-fold increase in the stability of E4I-subtilin in comparison to natural subtilin, which had a t$_{1/2}$ of only 0.8 days. The biological stability was determined by measuring the antimicrobial activity over the same time course using the spore outgrowth assay. FIG. 3 shows that the antimicrobial activity of the mutant subtilin dropped very little during the 48-day incubation period, showing that the biological stability was dramatically increased compared to natural subtilin. We conclude that the $Glu_4$ to Ile mutation caused a dramatic enhancement of the general stability of the subtilin molecule, both in terms of the chemical stability of the $DHA_5$ residue, and its biological activity.

E4I-subtilin in which $DHA_5$ mutated to Ala has no activity against spore outgrowth. If $DHA_5$ plays a critical role in the antimicrobial activity of subtilin, its mutation to another residue should result in a molecule that has no activity in the bacterial spore assay. It was decided that an appropriate experiment would involve mutation of the $DHA_5$ residue of E4I-subtilin to Ala (SEQ ID NO:9). Ala was chosen in order to retain the hydrophobicity of $DHA_5$ while destroying the double bond. E4I-subtilin was chosen in lieu of subtilin because of its greater inherent stability. E4I/DHA5A-subtilin (SEQ ID NO:10) was constructed using the mutagenic oligonucleotide shown in FIG. 6 (SEQ ID NO:11). The mutant was isolated in the same manner as subtilin and E4I-subtilin, and subjected to the complete range of tests for correct post-translational processing; including amino acid composition analysis, N-terminal sequence analysis, and NMR spectroscopy. The results established that all the post-translational steps occurred correctly. The biological activity of the E4I/DHA5A mutant subtilin was then determined in the bacterial spore outgrowth assay. Whereas E4I-subtilin inhibited spore outgrowth at a concentration of 0.3 µg/ml, the E4I/DHA5A subtilin was devoid of inhibitory activity against outgrowing spores, even at a concentration of 50 µg/ml, which is 150-fold higher than the concentration at which E4I-subtilin inhibits. Higher concentrations were not tested. We therefore conclude that an intact $DHA_5$ is critical for subtilin to inhibit spore outgrowth.

Accordingly, the E4I-subtilin of the claimed invention, identical to native subtilin saved for the substitution, at the 4 position, of an isoleucine residue, in place of the naturally-occurring glutamate residue (SEQ ID NO:7), yields an antibiotic 57-fold more stable than the natural version, with an increase in specific activity of 3–4 times the naturally expressed antibiotic. Other residues, which are inert to the deactivation of the dehydroalanine critical for activity at position 5, and which do not independently adversely affect the performance of the antibiotic, may be used to give similar results. The preparation of such analogs is a matter for empirical study which can be conducted according to the protocol set forth above.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An antibiotic having the amino acid sequence of native subtilin, save that the 4-position of the native sequence is substituted for by isoleucin.

2. An antibiotic exhibiting at least 10-fold superior stability, and 3-fold superior activity than native subtilin, and having the amino acid sequence of native subtilin except at the 4-position.

3. The antibiotic of claim 1, having the sequence of SEQ ID NO:23 prior to dehydration of serines and threonines and formation of thioether cross-linkages:

Trp Lys Ser Ile Ser Leu Cys Thr Pro Gly Cys Val Thr Gly Ala Leu Gln Thr Cys Phe Leu Gln Thr Leu Thr Cys Asn Cys Lys Ile Ser Lys.

4. The antibiotic of claim 1, having the sequence of SEQ ID NO:7 prior to dehydration of serines and threonines, formation of thioether cross-linkages and removal of the leader peptide:

Met Ser Lys Phe Asp Asp Phe Asp Leu Asp Val Val Lys Val Ser Lys Gln Asp Ser Lys Ile Thr Pro Gln Trp Lys Ser Ile Ser Leu Cys Thr Pro Gly Cys Val Thr Gly Ala Leu Gln Thr Cys Phe Leu Gln Thr Leu Thr Cys Asn Cys Lys Ile Ser Lys.

5. The antibiotic of claim 2, wherein said activity is inhibiting outgrowth of *Bacillus cereus* T spores, relative to native subtilin from *Bacillus subtilis* ATCC 6633.

6. The antibiotic of claim 2, having the sequence of SEQ ID NO:23 prior to dehydration of serines and threonines and formation of thioether cross-linkages:

&n

Met Ser Lys Phe Asp Asp Phe Asp Leu Asp Val Val Lys Val Ser
Lys Gln Asp Ser Lys Ile Thr Pro Gln Trp Lys Ser Ile Ser Leu
Cys Thr Pro Gly Cys Val Thr Gly Ala Leu Gln Thr Cys Phe Leu
Gln Thr Leu Thr Cys Asn Cys Lys Ile Ser Lys.

8. A modified subtilin having an isoleucine residue at the 4-position and exhibiting at least 10-fold superior stability and at least 3-fold superior activity in inhibiting outgrowth of *Bacillus cereus* T spores relative to native subtilin from *Bacillus subtilis* ATCC 6633.

9. The modified subtilin of claim 8, having the sequence of SEQ ID NO:23 prior to dehydration of serines and threonines and formation of thioether cross-linkages:

Trp Lys Ser Ile Ser Leu Cys Thr Pro Gly Cys Val Thr Gly Ala
Leu Gln Thr Cys Phe Leu Gln Thr Leu Thr Cys Asn Cys Lys Ile
Ser Lys.

10. The modified subtilin of claim 8, having the sequence of SEQ ID NO:7 prior to dehydration of serines and threonines, formation of thioether cross-linkages and removal of the leader peptide:

Met Ser Lys Phe Asp Asp Phe Asp Leu Asp Val Val Lys Val Ser
Lys Gln Asp Ser Lys Ile Thr Pro Gln Trp Lys Ser Ile Ser Leu
Cys Thr Pro Gly Cys Val Thr Gly Ala Leu Gln Thr Cys Phe Leu
Gln Thr Leu Thr Cys Asn Cys Lys Ile Ser Lys.

11. A modified subtilin having an isoleucine residue at the 4-position and exhibiting at least 10-fold superior stability and at least 3-fold superior antibiotic or antimicrobial activity relative to native subtilin from *Bacillus subtilis* ATCC 6633.

* * * * *